(12) United States Patent
Buchbinder et al.

(10) Patent No.: US 10,596,561 B2
(45) Date of Patent: Mar. 24, 2020

(54) HALOMETALLATE IONIC LIQUID MICRO-EMULSIONS

(71) Applicant: UOP LLC, Des Plaines, IL (US)

(72) Inventors: Avram M. Buchbinder, Skokie, IL (US); Hayim Abrevaya, Kenilworth, IL (US); Gavin P. Towler, Inverness, IL (US)

(73) Assignee: UOP LLC, Des Plaines, IL (US)

( * ) Notice: Subject to any disclaimer, the term of this patent is extended or adjusted under 35 U.S.C. 154(b) by 62 days.

(21) Appl. No.: 15/713,017

(22) Filed: Sep. 22, 2017

(65) Prior Publication Data

US 2018/0015448 A1  Jan. 18, 2018

Related U.S. Application Data

(63) Continuation of application No. PCT/US2016/025415, filed on Mar. 31, 2016.

(60) Provisional application No. 62/141,087, filed on Mar. 31, 2015.

(51) Int. Cl.
*B01J 31/02* (2006.01)
*B01J 35/00* (2006.01)
*C07C 2/00* (2006.01)

(52) U.S. Cl.
CPC ....... *B01J 31/0288* (2013.01); *B01J 31/0281* (2013.01); *B01J 31/0284* (2013.01); *B01J 31/0289* (2013.01); *B01J 35/0013* (2013.01); *C07C 2/00* (2013.01); *B01J 31/0277* (2013.01)

(58) Field of Classification Search
CPC ................ B01J 31/0277; B01J 31/0281; B01J 31/0284; B01J 31/0288; B01J 31/0289; B01J 35/0013; C07C 2/00
See application file for complete search history.

(56) References Cited

U.S. PATENT DOCUMENTS

| | | | |
|---|---|---|---|
| 7,553,406 B2 | 6/2009 | Wasserscheid et al. |
| 8,163,856 B2 | 4/2012 | Bergman et al. |
| 8,198,499 B2 | 6/2012 | Luo et al. |
| 8,535,650 B2 | 9/2013 | Constantinides et al. |
| 2005/0119423 A1 | 6/2005 | Bergman et al. |

(Continued)

FOREIGN PATENT DOCUMENTS

| | | |
|---|---|---|
| CN | 101274249 B | 3/2011 |
| CN | 101244972 B | 5/2012 |

(Continued)

OTHER PUBLICATIONS

Blahusiak, "Physical properties of phosponium ionic liquid and its mixtures with dodecane and water", J. Chem. Thermodynamics 93 (2016) 267-271.

(Continued)

*Primary Examiner* — Jun Li

(57) ABSTRACT

A micro-emulsion and a method of making the micro-emulsion are described. The micro-emulsion includes a hydrocarbon component, an ionic liquid component, and a co-solvent. The ionic liquid comprises a halometallate anion and a cation. The micro-emulsion can optionally include a surfactant, and a catalyst promoter. The co-solvent has a polarity greater than the polarity of the hydrocarbon. The ionic liquid is present in an amount of about 0.05 wt % to about 40 wt % of the micro-emulsion.

17 Claims, 3 Drawing Sheets

(56) References Cited

U.S. PATENT DOCUMENTS

| | | | |
|---|---|---|---|
| 2006/0120213 A1* | 6/2006 | Tonkovich | B01F 3/0807 366/144 |
| 2007/0142213 A1 | 6/2007 | Elomari et al. | |
| 2007/0142216 A1* | 6/2007 | Harris | B01J 27/125 502/53 |
| 2008/0241041 A1* | 10/2008 | Clothier | B82Y 30/00 423/263 |
| 2010/0197483 A1 | 8/2010 | Elomari et al. | |
| 2011/0217553 A1* | 9/2011 | Warner | B82Y 30/00 428/402.24 |
| 2012/0121485 A1 | 5/2012 | Rogers et al. | |
| 2013/0066130 A1 | 3/2013 | Luo et al. | |

FOREIGN PATENT DOCUMENTS

| | | |
|---|---|---|
| EP | 1920824 A1 | 5/2008 |
| RU | 46542 U1 | 7/2005 |
| WO | 1995021872 | 8/1995 |
| WO | 2003089390 A2 | 10/2003 |
| WO | 2006111712 A2 | 10/2006 |
| WO | 2006131699 A1 | 12/2006 |
| WO | 2010135064 A2 | 11/2010 |
| WO | 2012009031 A2 | 1/2012 |
| WO | 2013183137 A1 | 12/2013 |
| WO | 2016161197 A1 | 10/2016 |
| WO | 2016161199 A1 | 10/2016 |
| WO | 2016161200 A1 | 10/2016 |
| WO | 2016161202 A1 | 10/2016 |
| WO | 2016161203 A1 | 10/2016 |
| WO | 2016161204 A1 | 10/2016 |
| WO | 2016161206 A1 | 10/2016 |
| WO | 2016161208 A1 | 10/2016 |

OTHER PUBLICATIONS

Chandran, "Self-Assembled Inverted Micelles Stabilize Ionic Liquid Domains in Supercritical CO2", J. Am. Chem. Soc. 2010, 132, 12511-12516.

Cheng, "Self-Assembly of Imidazolium-Based Rodlike Ionic Liquid Crystals: Transition from Lamellar to Micellar Organization", Chem. Eur. J. 2010, 16, 4588-4601.

Chen, "Solubility measurements of isobutane/alkenes in sulfuric acid: applications to alkylation", Applied Catalysis A: General 255 (2003) 231-237.

Cong, "Isobutane/2-Butene Alkylation Catalyzed by Strong Acids in the Presence of Ionic Liquid Additives", Petroleum Science and Technology, 32:1981-1987, 2014.

Correa, "Nonaqueous Polar Solvents in Reverse Micelle Systems", Chem. Rev. 2012, 112, 4569-4602.

Eggers, "Enzymatic production of L-tryptophan in a reverse micelle reactor", Bioprocessing Engineering 3 (1988) 83-91.

Gayet, "Surfactant Aggregates in Ionic Liquids and Reactivity in Media", International Journal of Chemical Reactor Engineering (2010), vol. 8, 17 pages.

Huang, "Improved catalytic lifetime of H2SO4 for isobutane alkylation with trace amount of ionic liquids buffer", Industrial & Engineering Chemistry Research (2015), Web publication, 1-27.

Rai, "Ethanol-Assisted, Few Nanometer, Water-In-Ionic-Liquid Reverse Micelle Formation by a Zwitterionic Surfactant", Chem. Eur. J. 2012, 18, 12213-12217.

Rojas, "Nonaqueous Microemulsions Based on N,N'-Alkylimidazolium Alkylsulfate Ionic Liquids", Langmuir 2013, 29, 6833-6839.

Uskokovic, "Reverse micelles: Inert nano-reactors or physico-chemically active guides of the capped reactions", Advances in Colloid and Interface Science 133 (2007) 23-34.

Xue, "Choline acetate enhanced the catalytic performance of Candida rogusa lipase in AOT reverse micelles", Colloids and Surfaces B: Biointerfaces 105 (2013) 81-86.

Yang, "Study on Enzymatic Activity and Stability in Different Reaction Media", from Henan Huagong (2008), 25(9), 1-5. | Language: Chinese, Database: CAPLUS.

Zhao, "Liquid Crystalline Phases Self-Organized from a Surfactant-like Ionic Liquid C16mimCI in Ethylammonium Nitrate", J. Phys. Chem. B 2009, 113, 2024-2030.

Search Report dated Jun. 30, 2016 for corresponding PCT Appl. No. PCT/US2016/025415.

U.S. Appl. No. 62/141,056, filed Mar. 31, 2015.
U.S. Appl. No. 62/141,070, filed Mar. 31, 2015.
U.S. Appl. No. 62/141,076, filed Mar. 31, 2015.
U.S. Appl. No. 62/141,087, filed Mar. 31, 2015.

Li, "Compressed CO2-enhanced solubilization of 1-butyl-3-methylimidazolium tetrafluoroborate . . . " Journal of Chemical Physics (2004), 121(15), 7408-7412.

Li, "Nonaqueous microemulsion-containing ionic liquid [bmim][PF6] as polar microenvironment", Colloid and Polymer Science (2005), 283(12), 1371-1375.

Falcone, "On the formation of new reverse micelles: A comparative study of benzene/surfactants/ionic liquids . . . ", Langmuir (2009), 25(18), 10426-10429.

Moniruzzaman, "Formation of reverse micelles in a room-temperature ionic liquid", ChemPhysChem (2008), 9(5), 689-692.

International Search report for PCT/US2016/025411, dated Jul. 14, 2016.

International Search report for PCT/US2016/025414, dated Jul. 14, 2016.

International Search report for PCT/US2016/025421, dated Jun. 23, 2016.

International Search report for PCT/US2016/025419, dated Jun. 30, 2016.

International Search report for PCT/US2016/025425, dated Jul. 14, 2016.

International Search report for PCT/US2016/025429, dated Aug. 18, 2016.

International Search report for PCT/US2016/025422, dated Jun. 30, 2016.

International Search report for PCT/US2016/025415, dated Jun. 30, 2016.

* cited by examiner

HALOMETALLATE IONIC LIQUID MICRO-EMULSIONS

CROSS-REFERENCE TO RELATED APPLICATIONS

This application is a Continuation of copending International Application No. PCT/US2016/025415 filed Mar. 31, 2016, which application claims priority from U.S. Provisional Application No. 62/141,087 filed Mar. 31, 2015, the contents of which cited applications are hereby incorporated by reference in their entirety.

BACKGROUND OF THE INVENTION

In liquid-liquid reactions, an intrinsic tradeoff exists between reactivity and post-reaction separation. High interfacial surface area between two liquid phases is needed to achieve high activity. As an example, for motor fuel alkylation using ionic liquid catalysts, large ionic liquid droplets implies low surface area, which leads to slow mass transfer of olefin and isobutane from the bulk hydrocarbon phase to the ionic liquid droplets, and a mass transfer-limited reaction of olefin inside the ionic liquid droplets. Mass transfer limitations also lead to slow product mass transfer out of the ionic liquid droplets back to the hydrocarbon phase and to product degradation, hence to low $C_8$ alkylate selectivities.

High ionic liquid inventory and/or smaller ionic liquid droplets are used to counter the mass transfer limitations of the alkylation kinetics. However, smaller droplets which are typically generated by shear force, are also more difficult to separate than larger droplets once the reaction is complete. Small ionic liquid droplets require very long or even infinite settling times for complete separation by gravity. Often, specialized equipment such as coalescers or centrifugal separation may be employed. However, coalescers are subject to fouling by pinning of ionic liquid droplets on coalescing elements and separation by centrifugal force requires a large amount of power.

The high activity of ionic liquids used for motor fuel alkylation and related processes allows for the use of relatively low ionic liquid volume fractions compared to the high acid volume fractions used in HF or $H_2SO_4$ processes. However, even at low ratios of ionic liquid catalyst to hydrocarbon, the loss rates of ionic liquid due to inefficient separation and deactivation may introduce a significant cost in ionic liquid catalyst make-up.

Alternative methods for generating liquid-liquid mixtures which allow both efficient reaction and easy separation after the reaction is over are needed for alkylation and for other liquid-liquid reactions.

SUMMARY OF THE INVENTION

One aspect of the invention is a micro-emulsion. In one embodiment, the micro-emulsion comprises a hydrocarbon component comprising a hydrocarbon and an ionic liquid component comprising an ionic liquid. The micro-emulsion can include an optional surfactant, and an optional catalyst promoter. The co-solvent has a polarity greater than the polarity of the hydrocarbon. The ionic liquid comprises a halometallate anion and a cation, and the ionic liquid is present in an amount of about 0.05 wt % to about 40 wt % of the micro-emulsion.

Another aspect of the invention is a method of forming a micro-emulsion. In one embodiment, the method involves contacting the hydrocarbon, the co-solvent, the ionic liquid, the optional surfactant, and the optional catalyst promoter to form the micro-emulsion. The micro-emulsion comprises a hydrocarbon component comprising the hydrocarbon and an ionic liquid component comprising the ionic liquid. The co-solvent has a polarity greater than the polarity of the hydrocarbon. The ionic liquid comprises a halometallate anion and a cation. The ionic liquid is present in an amount of about 0.05 wt % to about 40 wt % of the micro-emulsion.

DETAILED DESCRIPTION OF THE INVENTION

Figure 1:
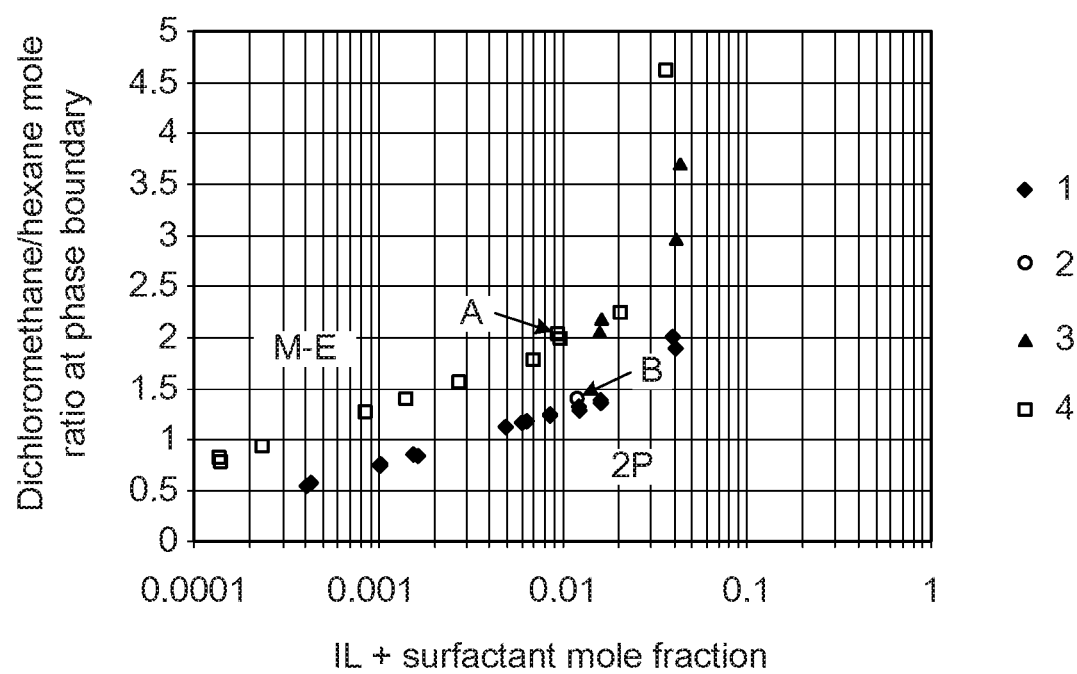
FIG. 1 is a phase diagram showing the dichloromethane/hexane mole ratio as a function of total ionic liquid plus surfactant mole fraction.

One aspect of the invention is a micro-emulsion composition composed at least partially of an ionic liquid in a mixture that contains a hydrocarbon. Rather than relying on the continuous input of force to shear the ionic liquid and create droplets, the micro-emulsion comprises thermodynamically stable structures in a less-polar medium. Although not wishing to be bound by theory, it is believed that the structures are stabilized by an amphiphilic surfactant or the ionic liquid itself.

The micro-emulsion contains a hydrocarbon component comprising a hydrocarbon having a polarity, an ionic liquid component comprising an ionic liquid, the ionic liquid comprising a halometallate anion and a cation, and a co-solvent having a polarity greater than the polarity of the hydrocarbon. The micro-emulsion can be reverse micelles, micelles, or a bi-continuous micro-emulsion. The ionic liquid component typically contains a higher content of co-solvent than the hydrocarbon component.

Reverse micelles are small structures containing an amphiphile, which allows for dispersion of a polar substance in a less-polar liquid. Such micro-emulsions are well known. Commonly, a micro-emulsion containing reverse micelles contains small structures on the order of one to tens of nanometers which consist of a water core surrounded by a surfactant in an organic solvent. Mixtures containing ionic liquid reverse micelles have been made. See, for example, Table 5 of Correa et al., Nonaqueous Polar Solvents in Reverse Micelle Systems, CHEM. REV. 2012, vol. 112, p. 4569-4602, which summarizes this work. Previous examples of ionic liquid reverse micelles generally contain a surfactant in addition to the ionic liquid. Furthermore, the prior art does not address the use of halometallate ionic liquids, which are often used in their Lewis acidic form. Such ionic liquids are very useful for catalytic applications including motor fuel alkylation, but they are also highly reactive and are not compatible with most protic or oxygenated solvents or surfactants.

In some embodiments of this invention, the micro-emulsion comprises reverse micelles. In these embodiments, the co-solvent is miscible in the hydrocarbon and at least a portion of the co-solvent is contained in the hydrocarbon component. The ionic liquid component is dispersed in the hydrocarbon component. The ionic liquid component is more polar than the hydrocarbon component.

In some embodiments, the micro-emulsion comprises micelles. With micelles, there is a core of the hydrocarbon component surrounded by the ionic liquid component and an optional surfactant. The hydrocarbon component core surrounded by the ionic liquid component and the optional surfactant is dispersed in a polar continuous medium which comprises the co-solvent. The co-solvent is more polar than the hydrocarbon component.

In some embodiments, the micro-emulsion comprises a bi-continuous micro-emulsion comprising the hydrocarbon component and the ionic liquid component. The ionic liquid component contains at least a portion of the co-solvent, and it is more polar than the hydrocarbon component.

In conventional liquid-liquid mixtures containing ionic liquids and hydrocarbons, where shear force is used to generate droplets in a two-phase mixture, ionic liquid solubility in the non-ionic liquid phase is typically very low. This can be characterized by the solubility of the ionic liquid in a typical non-polar hydrocarbon such as n-hexane. The ionic liquid has a solubility in n-hexane of less than about 5 wt %, or less than about 3 wt %, or less than about 1 wt %, or less than about 0.5 wt %, or less than about 0.1 wt %, or less than about 0.01 wt %. As an example, ionic liquids with halometallate anions have very low solubility in hydrocarbons such as n-hexane and are often characterized as immiscible with hexane, such as in Zhao, D; Wu, M; Kou, Y; Min, E, Catalysis Today, 2002, 74, 157-189 Table 2. As such, these ionic liquids do not form solutions or micro-emulsions when combined with non-polar hydrocarbons, but instead form two-phase systems, with the non-polar hydrocarbon phase being substantially free of ionic liquid. By substantially free we mean that the non-polar hydrocarbon phase contains less than about 5 wt %, or less than about 3 wt %, or less than about 1 wt %, or less than about 0.5 wt %, or less than about 0.1 wt %, or less than about 0.01 wt %. Therefore, in order to form a micro-emulsion, an additional component such as a surfactant and/or a co-solvent must be added. In the present invention, micro-emulsions can be made using an ionic liquid, a hydrocarbon, and a co-solvent. The micro-emulsion may optionally contain an additional surfactant and/or a catalyst promoter.

The hydrocarbon and co-solvent each have a polarity. The polarity of the co-solvent is greater than the polarity of the hydrocarbon. Many hydrocarbons, including those in some embodiments of this invention, have polarity close to zero. Many polarity scales are known. Here polarity is defined by the polarity index P', which is a measure of interactions of a solute relative to other solvents based on solubility constants. This polarity scale is commonly used to distinguish solvents by polarity for predicting solubility. Some hydrocarbons on this scale have P' less than zero. Hydrocarbons with P less than zero are considered to have polarity less than the polarity of the co-solvent if the co-solvent has P' greater than P' of the hydrocarbon. A detailed description of polarity index is found in Snyder, L. R; Journal of Chromatography, 1974, vol. 92, pp. 223-230 and tabulation of polarity index for many liquids is found in table I of that reference, which is incorporated herein by reference. For example, polarity index of n-hexane is 0.0, n-decane is −0.3, toluene is 2.3, benzene is 3.0, and methylene chloride (dichloromethane) is 3.4. In the absence of an available polarity index measurement, relative polarity of two liquids is determined from the magnitude of the liquids' dielectric constants. For instance, isobutane has dielectric constant of 1.8 at 300 K (Hayn, W. M, J. Chem. Eng. Data, 1983, vol. 28, pp. 367-369), while the dielectric constant of dichloromethane at 298 K is 9.14 (Dean, J. A; Lange's Handbook of Chemistry and Physics, 14$^{th}$ ed. p. 5.101, McGraw-Hill, 1992, New York).

In some embodiments, the micro-emulsion can be made utilizing a surfactant that is compatible with the ionic liquid, while in others, no additional surfactant is used. In the latter case, although not wishing to be bound by theory, it is believed that the ionic liquid itself acts as the amphiphile to stabilize the micro-emulsions. To generate a micro-emulsion using a hydrocarbon as a major component of the mixture, a polar aprotic co-solvent such as dichloromethane is used. The micro-emulsions are useful as high surface-area catalysts for alkylation and other hydrocarbon conversion processes, as well as separation processes.

Figure 2:
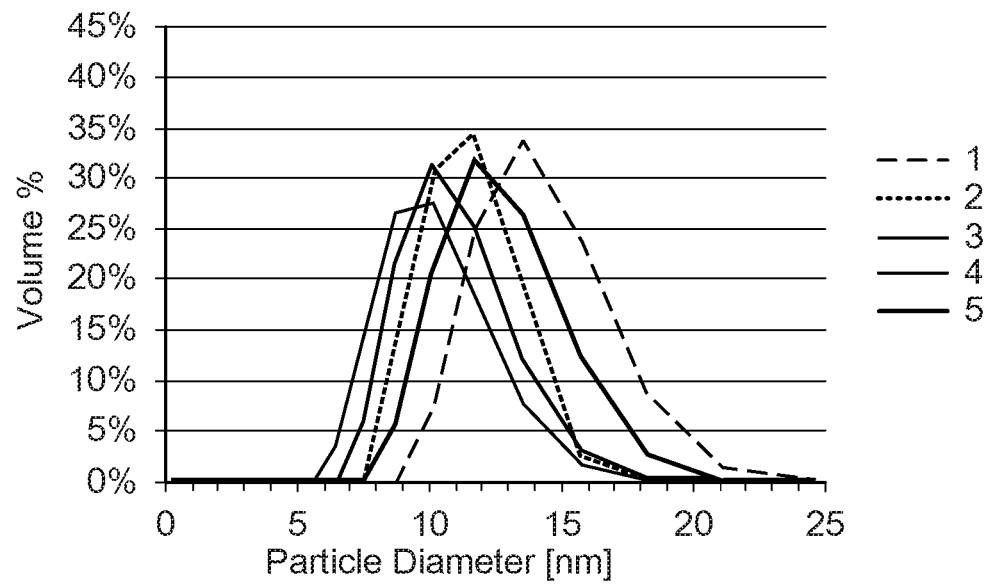
FIG. 2 is a graph showing the volume normalized particle size distribution of a composition containing reverse micelles made using an added surfactant.
Figure 3:
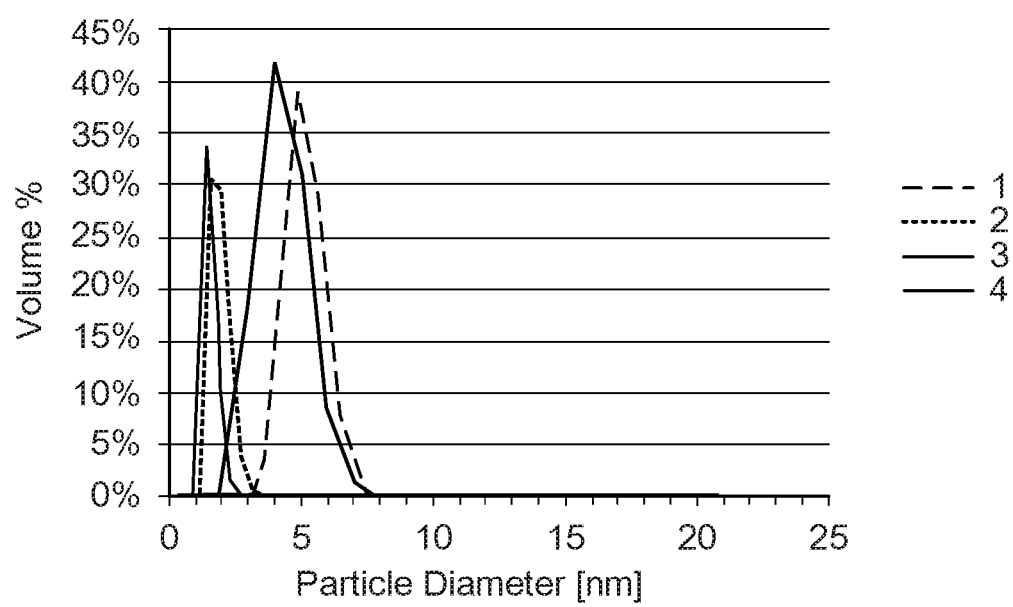
FIG. 3 is a graph showing the volume normalized particle size distribution of a composition containing reverse micelles made without an added surfactant.

In some embodiments, more than about 90% of the reverse micelles or micelles have a diameter less than about 100 nanometers, or less than about 90 nanometers, or less than about 80 nanometers, or less than about 70 nanometers, or less than about 60 nanometers, or less than about 50 nanometers, or less than about 40 nanometers, or less than about 30 nanometers, or less than about 20 nanometers, or about 1 nanometer to about 100 nanometers or about 1 nanometer to about 80 nanometers or about 1 nanometer to about 60 nanometers or about 1 nanometer to about 40 nanometers or about 1 nanometer to about 20 nanometers or about 1 nanometer to about 10 nanometers or about 1 nanometer to about 4 nanometers. The reverse micelles or micelles are typically at least about 1 nanometer in diameter. The presence of added surfactant can be used to help control the size of the reverse micelles or micelles, as shown in FIGS. 2-3. When an added surfactant is present, the reverse micelles or micelles may be larger. In some embodiments, reverse micelles or micelles with added surfactant have diameters about 2 to about 7 times larger than similar compositions without added surfactant. Not wishing to be bound by theory, the presence of an added surfactant may increase the surface tension of the reverse micelles or micelles and allow larger reverse micelles or micelles to be thermodynamically stable. In some embodiments, when an additional surfactant is present, more than about 90% of the reverse micelles or micelles have a diameter in the range of about 3 nanometers to about 100 nanometers, or about 3 nanometers to about 90 nanometers, or about 3 nanometers to about 80 nanometers, or about 3 nanometers to about 70 nanometers, or about 3 nanometers to about 60 nanometers, or about 3 nanometers to about 50 nanometers, or about 3 nanometers to about 40 nanometers, or about 3 nanometers to about 30 nanometers, or about 3 nanometers to about 20 nanometers, or about 5 nanometers to about 100 nanometers, or about 5 nanometers to about 90 nanometers, or about 5 nanometers to about 80 nanometers, or about 5 nanometers to about 70 nanometers, or about 5 nanometers to about 60 nanometers, or about 5 nanometers to about 50 nanometers, or about 5 nanometers to about 40 nanometers, or about 5 nanometers to about 30 nanometers, or about 5 nanometers to about 20 nanometers.

In some embodiments, the size distribution of the reverse micelles or micelles may be changed by changing the co-solvent. Not wishing to be bound by theory, using a more polar co-solvent may lead to larger reverse micelles or micelles due to the higher solubility of the co-solvent in the reverse micelles or micelles and due to the higher surface tension at the interface between the reverse micelles or micelles and the hydrocarbon component. The size of reverse micelles or micelles may also change if the co-solvent is modified to result in a different surface tension of the reverse micelles or micelles. For instance, a more polar co-solvent will often reduce the surface tension of micelles resulting in smaller structures.

The micro-emulsion is substantially free of water. The presence of water in the micro-emulsion is undesirable because it is not typically compatible with halometallate ionic liquids. Water reacts with the ionic liquid resulting in facile hydrolysis of the halometallate anion. In cases where the ionic liquid is Lewis acidic, this causes reduction in or neutralization of Lewis acidity. By substantially free of water, we mean that the reverse micelles or micelles themselves are not water, and the components in the micro-emulsion do not contain enough water to substantially affect the halometallate anion (i.e., it does not result in appreciable loss of activity for reactions that are catalyzed by the ionic liquid). There is typically less than about 300 wppm water in the micro-emulsion, or less than about 250 wppm water, or less than about 200 wppm water, or less than about 150 wppm water, or less than about 100 wppm water, or less than about 75 wppm water, or less than about 50 wppm water, or less than about 25 wppm water, or less than about 20 wppm water, or less than about 15 wppm water, or less than about 10 wppm water, or less than about 5 wppm water, or less than about 1 wppm water.

The ionic liquid comprises a cation and an anion. The cation is generally a nitrogen, phosphorous, or sulfur-based organic cation. In some embodiments, the cation is amphiphilic in nature and at least slightly soluble in the co-solvent. By "slightly soluble" we mean the cation is soluble in an amount of at least 0.5 mole ppm in the co-solvent. If the cation and anion are both not amphiphilic, an additional surfactant may be needed. In many cases, the ionic liquid is fully miscible with the co-solvent.

Suitable cations include, but are not limited to, nitrogen-based organic cations, phosphorus based organic cations, sulfur based cations, or combinations thereof. Examples of cations include tetraalkyl phosphoniums, dialkylimidazoliums, alkylimidazoliums, pyridiniums, alkyl pyridiniums, dialkyl pyridiniums, alkylpyrrolidiniums, dialkylpyrrolidiniums, trialkylammoniums, tetraalkylammoniums, lactamiums, alkyl-lactamiums and trialkylsulfoniums. Mixtures of cations may be used as well. Examples of suitable cations include, but are not limited to:

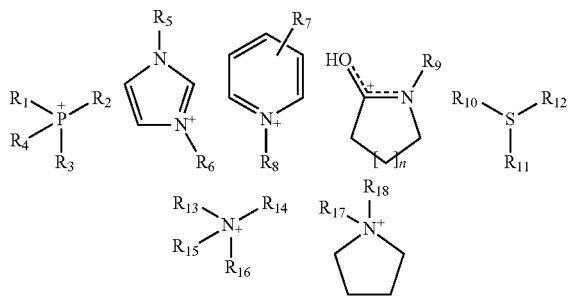

where $R_1$-$R_3$ are independently selected from alkyl groups, alkene groups, naphthene groups, and aryl groups having 1 to 12 carbon atoms, and $R_4$ is independently selected from alkyl groups, alkene groups, naphthene groups, and aryl groups having 1 to 15 carbon atoms; and where $R_5$-$R_{18}$ are independently selected from hydrogen, alkyl groups, alkene groups, naphthene groups, and aryl groups having 1 to 20 carbon atoms, n is 1 to 8, and the alkyl, naphthene, alkene and aryl groups may be substituted with halogens, or other alkyl, aryl and naphthene groups.

In some embodiments, the anion is a halometallate or anion with acidic character, and in most embodiments, with Lewis acidic character. In other embodiments, it can be neutral or basic in character. Halometallate anions may contain a metal selected from Al, Sc, Ti, V, Cr, Mn, Fe, Co, Ni, Cu, Zn, Ga, Y, Zr, Nb, Mo, In, Sn, Sb, La, Ce, Hf, Ta, W, or combinations thereof, and a halide selected from F, Cl, Br, I, or combination thereof. The halometallate may be a simple halometallate or a composite in which more than one metal is used. For catalytic applications requiring Lewis acidity (such as alkylation, disproportionation, reverse disproportionation, oligomerization, and isomerization), the ratio of moles of halide to moles of metal in the anion is less than 4. The anion may be formally an anion, or it may be an anion associated with a metal halide. For instance, the anion may be $AlCl_4^-$ associated with $AlCl_3$. In some embodiments, such as those where the ionic liquid comprises an imidazolium based cation, the ratio of moles of halide to moles of metal in the anion must be less than 4 in order for a micro-emulsion to form.

In embodiments in which the micro-emulsion contains reverse micelles, the hydrocarbon component is continuous and the ionic liquid component comprises reverse micelles that are dispersed in the hydrocarbon component. A majority of the hydrocarbon is in the hydrocarbon component. The co-solvent may be in the hydrocarbon component, the ionic liquid component, or both. In embodiments in which the micro-emulsion contains micelles, the hydrocarbon component forms the core of micellular structures which are surrounded by the ionic liquid component and optional surfactant. The micelles are dispersed in a continuous medium comprising the co-solvent.

The hydrocarbon comprises at least a part of the less polar hydrocarbon component of the micro-emulsion. A majority of the hydrocarbon is contained in the hydrocarbon component. The hydrocarbon may be a paraffin, an olefin, an aromatic, a naphthene, or mixtures of these. When micro-emulsions containing ionic liquid are used to catalyze a hydrocarbon conversion process, the hydrocarbon reactants also serve as a portion of the hydrocarbon component.

In order to form a micro-emulsion containing reverse micelles, there must be at least some solubility of the amphiphile in both the hydrocarbon component and the ionic liquid component of the micro-emulsion. Here, at least some solubility of the amphiphile in the hydrocarbon component is defined as the amphiphile being soluble in an amount of at least 0.5 mole ppm in the hydrocarbon component. If the cation and anion are both not amphiphilic, an additional surfactant may be needed to act as the amphiphile. The solubility of the ionic liquid or the optional surfactant in the ionic liquid component is generally much higher than in the hydrocarbon component and depends on the type of ionic liquid or the optional surfactant and size of the reverse micelles.

In cases where a non-polar hydrocarbon medium is desired (for instance, in motor fuel alkylation where the medium must contain isobutane), a co-solvent is used to modify the polarity of the hydrocarbon. The co-solvent is more polar than the hydrocarbon. The co-solvent must also be compatible with the ionic liquid and must be miscible with the hydrocarbon. Here, miscible with the hydrocarbon means that the co-solvent is soluble in an amount of at least 1 mol % in the hydrocarbon. Suitable co-solvents are any organic solvents containing at least one atom that is not carbon or hydrogen. Examples include, but are not limited to, halomethanes, other halogenated hydrocarbons, halocarbons, halogenated aromatics, or combinations thereof Halogenated hydrocarbons are any compounds that contain carbon, hydrogen, and a halogen atom or atoms. Halomethanes are any compounds of the formula $CH_{4-n}X_n$ where X is selected from F, Cl, Br, I, or a combination thereof. Halocarbons are any compounds that contain only carbon and one or more halogens. Halogenated aromatics are aromatic compounds containing one or more halogen atoms, such as chlorobenzene. Halomethanes, halocarbons, halogenated aromatics, and compounds with no hydrogen attached to the adjacent (beta) carbon atom are preferable to compounds with a beta hydrogen (such as halogenated hydrocarbons with more than one carbon) because of the potential to eliminate a halogen and a hydrogen to form a hydrogen halide and an olefin. Suitable co-solvents include, but are not limited to, chloroform, dichloromethane, chloromethane, chlorobenzene, dichlorobenzene, fluoromethane, difluoromethane, trifluoromethane, and 1-chloro-2,2-dimethylpropane.

In cases where the ionic liquid is not Lewis acidic or where a weaker Lewis acid is utilized, other co-solvents may be used that would otherwise be reactive with stronger Lewis acids. These include, but are not limited to, ethers (e.g., tetrahydrofuran, and diethyl ether), alcohols (e.g., butanol, propanol, and methanol), amides (e.g., dimethylformamide, and dimethylacetamide), esters (e.g., ethyl acetate), ketones (e.g., acetone), nitriles (e.g., acetonitrile), sulfoxides (e.g., dimethylsulfoxide), sulfones (e.g., sulfolane), or combinations thereof.

In some embodiments, the viscosity of the co-solvent is less than about 1 centipoise at 25° C. Preferably, the viscosity of the co-solvent is less than about 0.6 centipoise at 25° C. This may be advantageous if the micro-emulsion is used in a process, such as alkylation, for which high viscosity may not be desirable.

In some embodiments, no additional surfactant is needed because the ionic liquid itself acts as an amphiphile to make a stable micro-emulsion. However, if a non-amphiphilic ionic liquid is used or if the use of less co-solvent is desired, a surfactant may be added. The surfactant can be cationic, anionic, or neutral. The surfactant can be amphiphilic and non-protic (i.e., it does not contain an acidic H atom bound to N, O, or S). Protic surfactants with very weakly acidic protons such as ternary ammonium salts and cyclic amides may also be suitable. Many surfactants that are not reactive with the ionic liquid are suitable. Examples of classes of such surfactants include, but are not limited to, surfactants containing functional groups such as amphiphilic quaternary ammonium salts, ternary ammonium salts, phosphonium salts, sulfonate salts, phosphonate salts, di-substituted amides (e.g., amides of the formula R—(C=O)—NR$_2$, where R groups are generally alkyl or aryl groups but may be substituted as well), ethers, or glymes. Ideally, the anion of the quaternary ammonium salt, the ternary ammonium salt, or the phosphonium salt may be selected to match the anion of the ionic liquid or selected to be compatible with it. By compatible with the anion of the ionic liquid we mean that the anion of the additional surfactant does not neutralize the Lewis acidity of the ionic liquid anion or coordinate strongly to the ionic liquid anion such that the catalyst activity is substantially decreased. By substantially decreased we mean that the reaction rate for isobutane alkylation with olefins is decreased by more than 25% for a mole ratio of surfactant to ionic liquid of 1:1 compared to the same conditions with no additional surfactant. As an example of compatible surfactant anions, $Cl^-$, $AlCl_4^-$ or $Al_2Cl_7^-$ may be used as the anion with an $Al_2Cl_7^-$ ionic liquid (as may the bromide versions). Examples of cationic quaternary ammonium salts are cetyltrimethylammonium chloride, and benzyldimethyltetradecylammonium chloride. Anionic surfactants may also be suitable; however, most include sulfonate groups which are expected to be reactive with, or coordinate to, a Lewis acidic ionic liquid. Ideally, the cation of the sulfonate salt or phosphonate salt may be selected to match the cation of the ionic liquid or selected to be compatible with the cation of the ionic liquid. For instance, if the acidic ionic liquid is tributylhexylphosphonium heptachloroaluminate the surfactant could be tributylhexylphosphonium dodecyl sulfonate. As demonstrated below, the use of a surfactant allows use of a smaller quantity of polar co-solvent, and in some cases results in larger reverse micelles.

Another optional material is a catalyst promoter. In many hydrocarbon conversion reactions, such as motor fuel alkylation and paraffin disproportionation, a Brønsted acidic catalyst promoter is needed. Two common classes of promoters are anhydrous hydrogen halides (for instance, HCl) and halogenated hydrocarbons (such as 2-chlorobutane or 2-chloro-2-methyl propane (t-butyl chloride)). The halogenated hydrocarbons react in the presence of a Lewis acid to form a hydrogen halide and an olefin.

The above materials are mixed in specific ratios such as to stabilize ionic liquid micro-emulsions. The ionic liquid is typically present in an amount of about 0.05 wt % to about 40 wt % of the micro-emulsion, or about 0.05 wt % to about 35 wt %, or about 0.05 wt % to about 30 wt %, or about 0.05 wt % to about 25 wt %, or about 0.05 wt % to about 20 wt %, or about 0.05 wt % to about 15 wt %, or about 0.05 wt % to about 10 wt %, or about 0.05 wt % to about 5 wt %, or about 0.05 wt % to about 1 wt %.

The co-solvent is typically present in an amount of about 30 wt % to about 80 wt % of the micro-emulsion, or about 40 wt % to about 80 wt %, or about 30 wt % to about 70 wt %, or about 30 wt % to about 60 wt %, or about 40 wt % to about 70 wt %.

The amount of co-solvent needed is lower when less ionic liquid is present in the composition. The molar ratio of the surfactant to the ionic liquid is typically less than about 2.5:1, or less than about 1.5:1.

When the catalyst promoter is present, the molar ratio of the catalyst promoter to the ionic liquid is typically about 0.1:1 to about 1:1, or about 0.1:1 to about 0.7:1, or about 0.2:1 to about 0.7:1.

The amounts of co-solvent and surfactant needed to stabilize the micro-emulsion depend on the amount of ionic liquid and hydrocarbon component present. When surfactant is included in the micro-emulsion, generally less co-solvent is needed. When more ionic liquid is included in the micro-emulsion, generally more surfactant or more co-solvent is needed.

The amounts of each material needed to result in a stable micro-emulsion may be determined by determination of a phase diagram. The phase diagram for a given combination of hydrocarbon, co-solvent, ionic liquid, optional surfactant and catalyst promoter is constructed by preparing mixtures containing various known amounts of the materials. A particular composition is then determined to be a micro-emulsion or consist of two distinct phases. Determination of whether a composition is a micro-emulsion or two distinct phases is generally completed by assessing turbidity of the mixture or identifying an interface between two phases, but may be accomplished by other means known in the art such as dynamic light scattering, conductivity measurement, or x-ray scattering. A mixture which is a micro-emulsion is then subjected to addition of the hydrocarbon or ionic liquid to determine the composition at which the phase boundary between micro-emulsion and two-phase composition exists. Alternatively, a mixture which is two phases is subjected to addition of co-solvent or surfactant to determine the composition at which the phase boundary between micro-emulsion and two-phase composition exists.

The micro-emulsion can be formed by contacting or otherwise mixing the hydrocarbon, the co-solvent, the ionic liquid, the optional surfactant, and the optional catalyst promoter. The hydrocarbon has a polarity less than the polarity of the co-solvent. In some embodiments, the co-solvent is miscible in the hydrocarbon, at least up to the desired composition. The ionic liquid comprises a halometallate anion and a cation. In some embodiments, the ionic liquid is at least slightly soluble in the co-solvent. By slightly soluble, we mean that at least 1 wt % of the ionic liquid is soluble in the co-solvent. The ionic liquid is present in an amount of about 0.05 wt % to about 40 wt % of the micro-emulsion.

The materials can be combined in different ways. For example, the hydrocarbon and co-solvent can be combined first, and then combined with ionic liquid. Alternatively, the ionic liquid and the co-solvent can be combined first, and then combined with the hydrocarbon. The optional surfactant and optional catalyst promoter can be added at different times and to different combinations of the materials. For example, the catalyst promoter and optional surfactant can be added to the hydrocarbon, the co-solvent, the ionic liquid, or any combinations of these materials. In another alternative, all of the materials could be combined at the same time. Other ways of combining the materials would be understood by those skilled in the art.

In one method, an ionic liquid and an optional surfactant are dissolved in a co-solvent to form the ionic liquid component. The ionic liquid comprises a halometallate anion and a cation. The ionic liquid component is introduced into a hydrocarbon to form the micro-emulsion. The polarity of the hydrocarbon is less than the polarity of the co-solvent, and the co-solvent is miscible in the hydrocarbon. The hydrocarbon component comprises the hydrocarbon and the co-solvent. The ionic liquid is present in an amount of about 0.05 wt % to about 40 wt % of the micro-emulsion. If a catalyst promoter is included, it can be added to the ionic liquid component, the hydrocarbon, the co-solvent, or the micro-emulsion.

Another method involves mixing the hydrocarbon with a co-solvent to form a hydrocarbon component. The polarity of the hydrocarbon is less than the polarity of the co-solvent, and the co-solvent is miscible in the hydrocarbon. The ionic liquid and an optional surfactant are added to the hydrocarbon component to form the micro-emulsion. The ionic liquid is present in an amount of about 0.05 wt % to about 40 wt % of the micro-emulsion. If a catalyst promoter is included, it can be added to the hydrocarbon, the co-solvent, the ionic liquid, or the micro-emulsion.

Processes using ionic liquid micro-emulsions are described in U.S. Application No. 62/141,056; U.S. Application No. 62/141,070; and U.S. Application No. 62/141,076, all filed on Mar. 31, 2015, each of which is incorporated herein by reference.

EXAMPLES

Example 1

In the examples below, n-hexane is used as the hydrocarbon, tributylhexylphosphonium heptachloroaluminate is used as the ionic liquid, and dichloromethane is used as the co-solvent.

Micro-emulsions were generated by preparing a mixture of ionic liquid and (in some cases) benzyldimethyltetradecylammonium chloride, referred to as "surfactant" below. Four different compositions were prepared with the following surfactant:ionic liquid mole ratios. Formulation 1 had a molar ratio of surfactant:ionic liquid of 2.1:1. Formulation 2 had a molar ratio of surfactant:ionic liquid of 1.7:1. Formulation 3 had a molar ratio of surfactant:ionic liquid of 0.83:1. Formulation 4 had no surfactant. Sufficient dichloromethane was added to dissolve the ionic liquid and surfactant. Following this, n-hexane was added dropwise, with shaking. When turbidity appeared, this composition was recorded as the boundary between the micro-emulsion region and the two-phase region of the phase diagram. A drop or drops of dichloromethane was then added to check that cloudiness disappeared. This was recorded as a second limit for the phase boundary. Additional dichloromethane was added, and the procedure was repeated. As the ionic liquid and surfactant became more dilute in the mixture, less dichloromethane was needed in the mixture to clarify the liquid. When a large amount of surfactant was added to the ionic liquid, less dichloromethane was needed to stabilize the same amount of ionic liquid. However, with little or no surfactant a phase boundary was also found. A phase diagram showing the required dichloromethane/hexane ratio to form a clear liquid (the phase boundary) for each of the formulations 1-4 as a function of total ionic liquid plus surfactant mole fraction is shown in FIG. 1.

The micro-emulsion region (M-E) is above and to left of the phase boundary while the two phase region (2P) is below and to the right of the phase boundary. Micro-emulsions are broken to produce two phases when the composition is changed from a composition in the micro-emulsion region to the two phase region. A list of compositions measured which were on the phase boundary are in Table 1.

Example 2

Compositions that were sufficiently cloudy and contained sufficient amounts of ionic liquid would eventually settle to form two liquid phases, indicating that cloudiness was due to formation of a second liquid phase. In mixtures that were not cloudy, formation of a micro-emulsion was presumed. This was confirmed by measuring particle size by dynamic light scattering (DLS) using a Zetasizer Nano ZS two angle particle and molecular size analyzer (Malvern Instruments LTD., UK) for two compositions, one with and one without additional surfactant. Compositions were prepared as described in Example 1. A composition was prepared with 2.9 wt % tributylhexylphosphonium heptachloroaluminate ionic liquid, 2.9 wt % benzyldimethyltetradecylammonium chloride, 54.6 wt % dichloromethane and 39.5 wt % hexane. The micro-emulsion was placed in a quartz cuvette (1 cm path length) with a Teflon stopper. Particle size distributions were measured using the analyzer's particle size mode. 30 scans were collected for each sample assuming viscosity of 0.347 centipoise (the volume weighted average viscosity of n-hexane and dichloromethane in the mixture) of the continuous phase, and refractive index of 1.403 (the volume weighted average refractive index of n-hexane and dichloromethane in the mixture). This composition had measured volume normalized average particle size of 12±2 nm. This composition is indicated with a "B" on FIG. 1. Volume normalized particle size distributions for five repeat measurements (1-5) are shown in FIG. 2.

A composition with 6.16 wt % tributylhexylphosphonium heptachloroaluminate ionic liquid, 62.7 wt % dichloromethane and 31.2 wt % hexane had measured particle size of 3±2 nm. This composition is indicated with an "A" on FIG. 1. Volume normalized particle size distributions for four repeat measurements (1-4) are shown in FIG. 3. The size of the particles is more than three orders of magnitude smaller than droplets generated by impellers.

TABLE 1

Compositions on phase boundary between micro-emulsion and two-phase mixture for compositions containing tributylhexylphosphonium heptachloroaluminate as the IL, benzyldimethyltetradecylammonium chloride as the surfactant, dichloromethane and n-hexane

| IL wt % | Surfactant wt % | Dichloromethane wt % | Hexane wt % | Average size by DLS |
|---|---|---|---|---|
| 0.00% | 2.83% | 26.5% | 70.7% | |
| 0.00% | 2.73% | 25.6% | 71.7% | |
| 0.00% | 2.78% | 26.0% | 71.2% | |
| 20.78% | 0.00% | 64.9% | 14.3% | |
| 6.27% | 0.00% | 62.0% | 31.7% | |
| 6.16% | 0.00% | 62.7% | 31.2% | 3 nm |
| 12.66% | 0.00% | 60.1% | 27.2% | |
| 4.61% | 0.00% | 60.8% | 34.6% | |
| 1.83% | 0.00% | 59.5% | 38.7% | |
| 0.97% | 0.00% | 57.3% | 41.7% | |
| 0.96% | 0.00% | 57.5% | 41.6% | |
| 0.58% | 0.00% | 55.1% | 44.3% | |
| 0.58% | 0.00% | 55.5% | 43.9% | |
| 0.16% | 0.00% | 47.9% | 52.0% | |
| 0.10% | 0.00% | 43.4% | 56.5% | |
| 0.09% | 0.00% | 44.9% | 55.0% | |
| 13.68% | 6.84% | 62.4% | 17.1% | |
| 13.11% | 6.56% | 59.8% | 20.5% | |
| 5.73% | 2.87% | 62.4% | 29.0% | |
| 5.63% | 2.82% | 61.3% | 30.3% | |
| 7.84% | 9.80% | 53.6% | 28.8% | |
| 7.59% | 9.49% | 55.1% | 27.8% | |
| 7.72% | 9.65% | 54.3% | 28.3% | |
| 3.39% | 4.24% | 52.8% | 39.5% | |
| 3.35% | 4.19% | 53.4% | 39.1% | |
| 3.37% | 4.21% | 53.1% | 39.3% | |
| 2.61% | 3.26% | 52.6% | 41.5% | |
| 2.58% | 3.23% | 53.1% | 41.1% | |
| 1.86% | 2.33% | 52.5% | 43.3% | |
| 1.85% | 2.31% | 52.9% | 42.9% | |
| 1.39% | 1.74% | 52.0% | 44.9% | |
| 1.32% | 1.65% | 52.0% | 45.0% | |
| 1.07% | 1.34% | 51.3% | 46.3% | |
| 1.07% | 1.34% | 51.3% | 46.3% | |
| 1.07% | 1.34% | 51.3% | 46.3% | |
| 0.36% | 0.45% | 45.0% | 54.2% | |
| 0.34% | 0.42% | 45.4% | 53.9% | |
| 0.23% | 0.28% | 42.1% | 57.3% | |
| 0.23% | 0.28% | 42.6% | 56.8% | |
| 0.10% | 0.12% | 36.3% | 63.5% | |
| 0.09% | 0.11% | 34.4% | 65.4% | |
| 0.09% | 0.11% | 35.0% | 64.8% | |
| 2.94% | 2.94% | 54.6% | 39.5% | 12 nm |

Example 3

In the examples below, n-hexane is used as the hydrocarbon, and dichloromethane is used as the co-solvent. Four different ionic liquids were tested: tributylhexylphosphonium-$Al_2Cl_7$ was used in formulation 1, tributylmethylphosphonium-$Al_2Cl_7$ was used in formulation 2, 1-butyl-3-methylimidazolilum-$Al_2Cl_7$ was used in formulation 3 and caprolactamium-$Al_2Cl_7$ was used in formulation 4.

Figure 4:
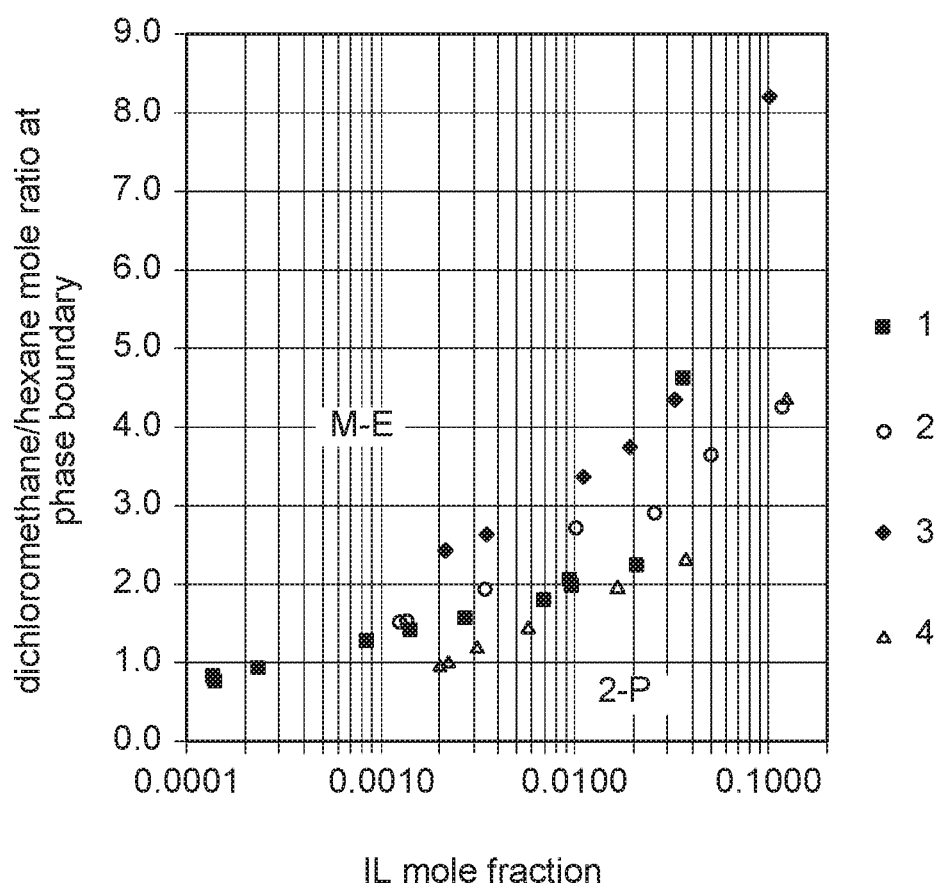
FIG. 4 is a phase diagram showing the dichloromethane/hexane mole ratio as a function of the ionic liquid mole fraction for various ionic liquids

Micro-emulsions were generated by preparing a mixture of ionic liquid and sufficient dichloromethane to dissolve the ionic liquid and surfactant. Following this, n-hexane was added dropwise, with shaking. When turbidity appeared, this composition was recorded as the boundary between the micro-emulsion region and the two-phase region of the phase diagram. A drop or drops of dichloromethane was then added to check that cloudiness disappeared. This was recorded as a second limit for the phase boundary. Additional dichloromethane was added, and the procedure was repeated. As the ionic liquid became more dilute in the mixture, less dichloromethane was needed in the mixture to clarify the liquid. A phase diagram showing the required dichloromethane/hexane ratio to form a clear liquid (the phase boundary) for each of the formulations 1-4 as a function of total ionic liquid mole fraction is shown in FIG. 4. The micro-emulsion region (M-E) is above and to left of the phase boundary while the two phase region (2P) is below and to the right of the phase boundary. Micro-emulsions are broken to produce two phases when the composition is changed from a composition in the micro-emulsion region to the two phase region. A list of compositions measured which were on the phase boundary are in Table 2.

TABLE 2

Compositions on phase boundary between micro-emulsion and two-phase mixture for compositions containing dichloromethane, hexane and four different ionic liquids.

| | IL wt % | DCM wt % | Hexane wt % | IL mol fraction | DCM/hexane mole fraction |
|---|---|---|---|---|---|
| TBHP-$Al_2Cl_7$ | 21% | 64.94% | 14.29% | 3.65E-02 | 4.61 |
| | 6.3% | 61.99% | 31.73% | 9.60E-03 | 1.98 |
| | 6.2% | 62.68% | 31.16% | 9.41E-03 | 2.04 |
| | 12.7% | 60.13% | 27.22% | 2.05E-02 | 2.24 |
| | 4.6% | 60.83% | 34.56% | 6.95E-03 | 1.79 |
| | 1.8% | 59.49% | 38.68% | 2.70E-03 | 1.56 |
| | 1.0% | 57.32% | 41.72% | 1.41E-03 | 1.39 |
| | 1.0% | 57.46% | 41.58% | 1.41E-03 | 1.40 |
| | 0.6% | 55.09% | 44.33% | 8.50E-04 | 1.26 |
| | 0.578% | 55.50% | 43.92% | 8.42E-04 | 1.28 |
| | 0.159% | 47.87% | 51.97% | 2.31E-04 | 0.93 |
| | 0.096% | 43.45% | 56.45% | 1.39E-04 | 0.78 |
| | 0.093% | 44.90% | 55.01% | 1.36E-04 | 0.83 |
| TBMP-$Al_2Cl_7$ | 45% | 44.53% | 10.63% | 1.18E-01 | 4.25 |
| | 24% | 59.09% | 16.42% | 5.05E-02 | 3.65 |
| | 14% | 63.73% | 22.34% | 2.59E-02 | 2.90 |
| | 6% | 68.44% | 25.67% | 1.02E-02 | 2.71 |
| | 2.0% | 64.20% | 33.75% | 3.43E-03 | 1.93 |
| | 0.8% | 59.67% | 39.51% | 1.36E-03 | 1.53 |
| | 0.8% | 59.49% | 39.76% | 1.24E-03 | 1.52 |
| BMIm-$Al_2Cl_7$ | 36.9% | 56.19% | 6.95% | 1.01E-01 | 8.21 |
| | 14.9% | 68.99% | 16.12% | 3.27E-02 | 4.34 |
| | 9.2% | 71.42% | 19.38% | 1.92E-02 | 3.74 |
| | 5.5% | 72.58% | 21.91% | 1.11E-02 | 3.36 |
| | 5.5% | 72.58% | 21.91% | 1.11E-02 | 3.36 |
| | 1.8% | 70.85% | 27.36% | 3.49E-03 | 2.63 |
| | 1.1% | 69.70% | 29.21% | 2.14E-03 | 2.42 |
| Caprolactamium-$Al_2Cl_7$ | 40.6% | 48.25% | 11.19% | 1.22E-01 | 4.38 |
| | 15.7% | 58.70% | 25.64% | 3.66E-02 | 2.32 |
| | 7.5% | 60.46% | 32.07% | 1.63E-02 | 1.91 |
| | 7.5% | 60.46% | 32.07% | 1.63E-02 | 1.91 |
| | 2.7% | 56.68% | 40.60% | 5.69E-03 | 1.42 |
| | 1.5% | 53.51% | 45.00% | 3.08E-03 | 1.21 |
| | 1.1% | 49.66% | 49.28% | 2.19E-03 | 1.02 |
| | 0.9% | 48.32% | 50.73% | 1.96E-03 | 0.97 |

As used herein, the term about means within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

Specific Embodiments

While the following is described in conjunction with specific embodiments, it will be understood that this description is intended to illustrate and not limit the scope of the preceding description and the appended claims.

A first embodiment of the invention is a micro-emulsion comprising a hydrocarbon component comprising a hydrocarbon having a polarity; an ionic liquid component comprising an ionic liquid, the ionic liquid comprising a halometallate anion and a cation; a co-solvent having a polarity greater than the polarity of the hydrocarbon; an optional surfactant; and an optional catalyst promoter; wherein the ionic liquid is present in an amount of about 0.05 wt % to about 40 wt % of the micro-emulsion. An embodiment of the invention is one, any or all of prior embodiments in this paragraph up through the first embodiment in this paragraph wherein the ionic liquid is present in an amount of about 0.05 wt % to about 25 wt % of the micro-emulsion. An embodiment of the invention is one, any or all of prior embodiments in this paragraph up through the first embodiment in this paragraph wherein the micro-emulsion comprises micelles or reverse micelles and wherein more than about 90% of the micelles or reverse micelles have a diameter less than about 100 nanometers. An embodiment of the invention is one, any or all of prior embodiments in this paragraph up through the first embodiment in this paragraph wherein the micro-emulsion comprises reverse micelles, wherein the co-solvent is miscible in the hydrocarbon, wherein the hydrocarbon component further comprises the co-solvent, and wherein ionic liquid component is dispersed in the hydrocarbon component. An embodiment of the invention is one, any or all of prior embodiments in this paragraph up through the first embodiment in this paragraph wherein the micro-emulsion comprises micelles, wherein the hydrocarbon component is surrounded by the ionic liquid component, and wherein the hydrocarbon component surrounded by the ionic liquid component is dispersed in the co-solvent. An embodiment of the invention is one, any or all of prior embodiments in this paragraph up through the first embodiment in this paragraph wherein the micro-emulsion comprises a bi-continuous phase, and wherein the ionic liquid component contains at least a portion of the co-solvent. An embodiment of the invention is one, any or all of prior embodiments in this paragraph up through the first embodiment in this paragraph wherein the micro-emulsion contains less than about 300 wppm of water. An embodiment of the invention is one, any or all of prior embodiments in this paragraph up through the first embodiment in this paragraph wherein the cation of the ionic liquid comprises a tetraalkyl phosphonium cation, a dialkylimidazolium cation, an alkylimidazolium cation, a pyridinium cation, an alkyl pyridinium cation, a dialkylpyridinium cation, an alkylpyrrolidinium cation, a dialkylpyrrolidinium cation, a trialkylammonium cation, a tetraalkylammonium cation, a lactamium cation, an alkyl-lactamium cation, a trialkylsulfonium cation, or combinations thereof. An embodiment of the invention is one, any or all of prior embodiments in this paragraph up through the first embodiment in this paragraph wherein the cation of the ionic liquid comprises at least one of

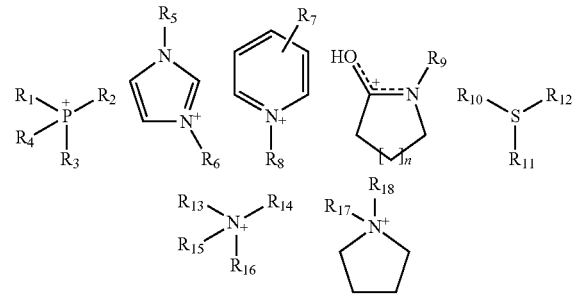

where $R_1$-$R_3$ are independently selected from alkyl groups, alkene groups, naphthene groups, and aryl groups having 1 to 12 carbon atoms, and $R_4$ is independently selected from alkyl groups, alkene groups, naphthene groups, and aryl groups having 1 to 15 carbon atoms; and where $R_5$-$R_{18}$ are independently selected from hydrogen, alkyl groups, alkene groups, naphthene groups, and aryl groups having 1 to 20 carbon atoms, n is 1 to 8, and the alkyl, naphthene, alkene and aryl groups may be substituted with halogens, or other alkyl, aryl and naphthene groups. An embodiment of the invention is one, any or all of prior embodiments in this paragraph up through the first embodiment in this paragraph wherein the halometallate anion contains a metal selected from Al, Sc, Ti, V, Cr, Mn, Fe, Co, Ni, Cu, Zn, Ga, Y, Zr, Nb, Mo, In, Sn, Sb, La, Ce, Hf, Ta, W, or combinations thereof, and a halide selected from F, Cl, Br, I, or combinations thereof. An embodiment of the invention is one, any or all of prior embodiments in this paragraph up through the first embodiment in this paragraph wherein the ionic liquid is acidic. An embodiment of the invention is one, any or all of prior embodiments in this paragraph up through the first embodiment in this paragraph wherein when the surfactant is present, the hydrocarbon comprises a paraffin, an olefin, a cycloalkane, or combinations thereof; and when the surfactant is not present, the hydrocarbon comprises a paraffin, an olefin, a cycloalkane, an aromatic, or combinations thereof. An embodiment of the invention is one, any or all of prior embodiments in this paragraph up through the first embodiment in this paragraph wherein the co-solvent comprises a halogenated hydrocarbon, a halocarbon, a halogenated aromatic, or combinations thereof. An embodiment of the invention is one, any or all of prior embodiments in this paragraph up through the first embodiment in this paragraph wherein the co-solvent comprises chloroform, dichloromethane, chloromethane, chlorobenzene, a dichlorobenzene, fluoromethane, difluoromethane, trifluoromethane, 1-chloro-2,2-dimethylpropane, or combinations thereof. An embodiment of the invention is one, any or all of prior embodiments in this paragraph up through the first embodiment in this paragraph wherein the co-solvent comprises an ether, an alcohol, an amide, an ester, a ketone, a nitrile, a sulfoxide, a sulfone or combinations thereof. An embodiment of the invention is one, any or all of prior embodiments in this paragraph up through the first embodiment in this paragraph wherein the surfactant is present and wherein the surfactant comprises a quaternary ammonium salt, a ternary ammonium salt, a phosphonium salt, a sulfonate salt, a sulfate salt, a phosphonate salt, a phosphate salt, a disubstituted amide, an ether, or a glyme. An embodiment of the invention is one, any or all of prior embodiments in this paragraph up through the first embodiment in this paragraph wherein an anion of the quaternary ammonium salt, the ternary ammonium salt, or the phosphonium salt is the same as the halometallate anion or is compatible with the halometallate anion, or wherein a cation of the sulfonate salt, the sulfate salt, the phosphate salt or phosphonate salt is the same as the cation of the ionic liquid or is compatible with the cation of the ionic liquid. An embodiment of the invention is one, any or all of prior embodiments in this paragraph up through the first embodiment in this paragraph wherein the catalyst promoter is present, and wherein the catalyst promoter comprises an anhydrous hydrogen halide, a halogenated hydrocarbon, or combinations thereof. An embodiment of the invention is one, any or all of prior embodiments in this paragraph up through the first embodiment in this paragraph wherein the co-solvent is present in an amount of about 30 wt % to about 80 wt % of the micro-emulsion. An embodiment of the invention is one, any or all of prior embodiments in this paragraph up through the first embodiment in this paragraph wherein the surfactant is present and wherein a molar ratio of the surfactant to the ionic liquid is less than about 2.5:1; or wherein the catalyst promoter is present, and wherein a molar ratio of the catalyst promoter to the ionic liquid is about 0.1:1 to about 1:1; or both.

A second embodiment of the invention is a method of forming a micro-emulsion comprising contacting a hydrocarbon, a co-solvent, an ionic liquid, an optional surfactant, and an optional catalyst promoter to form the micro-emulsion, the micro-emulsion comprising a hydrocarbon component comprising the hydrocarbon and an ionic liquid component comprising the ionic liquid, the ionic liquid comprising a halometallate anion and a cation, the co-solvent having a polarity greater than a polarity of the hydrocarbon, the ionic liquid being present in an amount of about 0.05 wt % to about 40 wt % of the micro-emulsion.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A micro-emulsion comprising:
a hydrocarbon component comprising a hydrocarbon having a polarity;
an ionic liquid component comprising an ionic liquid, the ionic liquid comprising a halometallate anion and a cation, wherein the ionic liquid does not contain fluorine;
a co-solvent having a polarity greater than the polarity of the hydrocarbon, wherein the co-solvent is miscible in the hydrocarbon, and wherein the co-solvent is present in an amount of about 30 wt % to about 80 wt % of the micro-emulsion;
a surfactant, wherein a molar ratio of the surfactant to the ionic liquid is less than 2.5:1; and
a catalyst promoter, wherein a molar ratio of the catalyst promoter to the ionic liquid is 0.1:1 to 1:1;
wherein the ionic liquid is present in an amount of about 0.05 wt % to about 40 wt % of the micro-emulsion; and
wherein the micro-emulsion comprises micelles or reverse micelles and wherein more than about 90% of the micelles or reverse micelles have a diameter less than about 100 nanometers.

2. The micro-emulsion of claim 1 wherein the ionic liquid is present in an amount of about 0.05 wt % to about 25 wt % of the micro-emulsion.

3. The micro-emulsion of claim 1 wherein the micro-emulsion comprises reverse micelles, wherein the hydrocarbon component further comprises the co-solvent, and wherein ionic liquid component is dispersed in the hydrocarbon component.

4. The micro-emulsion of claim 1 wherein the micro-emulsion comprises micelles, wherein the hydrocarbon component is surrounded by the ionic liquid component, and wherein the hydrocarbon component surrounded by the ionic liquid component is dispersed in the co-solvent.

5. The micro-emulsion of claim 1 wherein the micro-emulsion comprises a bi-continuous phase, and wherein the ionic liquid component contains at least a portion of the co-solvent.

6. The micro-emulsion of claim 1 wherein the micro-emulsion contains less than about 300 wppm of water.

7. The micro-emulsion of claim 1 wherein the cation of the ionic liquid comprises a tetraalkyl phosphonium cation, a dialkylimidazolium cation, an alkylimidazolium cation, a pyridinium cation, an alkyl pyridinium cation, a dialkylpyridinium cation, an alkylpyrrolidinium cation, a dialkylpyrrolidinium cation, a trialkylammonium cation, a tetraalkylammonium cation, a lactamium cation, an alkyl-lactamium cation, a trialkylsulfonium cation, or combinations thereof.

8. The micro-emulsion of claim 1 wherein the cation of the ionic liquid comprises at least one of

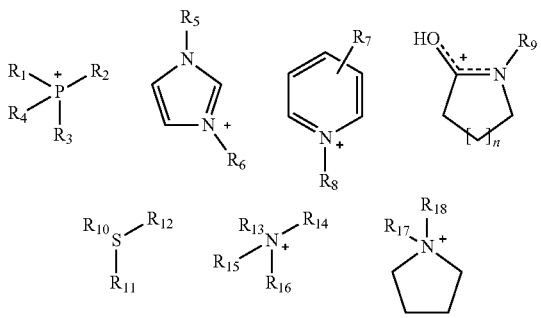

where $R_1$-$R_3$ are independently selected from alkyl groups, alkene groups, naphthene groups, and aryl groups having 1 to 12 carbon atoms, and $R_4$ is independently selected from alkyl groups, alkene groups, naphthene groups, and aryl groups having 1 to 15 carbon atoms; and where $R_5$-$R_{18}$ are independently selected from hydrogen, alkyl groups, alkene groups, naphthene groups, and awl groups having 1 to 20 carbon atoms, n is 1 to 8, and the alkyl, naphthene, alkene and aryl groups may be substituted with halogens other than fluorine, or other alkyl, aryl and naphthene groups.

9. The micro-emulsion of claim 1 wherein the halometallate anion contains a metal selected from Al, Sc, Ti, V, Cr, Mn, Fe, Co, Ni, Cu, Zn, Ga, Y, Zr, Nb, Mo, In, Sn, Sb, La, Ce, Hf, Ta, W, or combinations thereof, and a halide selected from Cl, Br, I, or combinations thereof.

10. The micro-emulsion of claim 1, the hydrocarbon comprises a paraffin, an olefin, a cycloalkane, or combinations thereof.

11. The micro-emulsion of claim 1 wherein the co-solvent comprises a halogenated hydrocarbon, a halocarbon, a halogenated aromatic, or combinations thereof.

12. The micro-emulsion of claim 1 wherein the co-solvent comprises chloroform, dichloromethane, chloromethane, chlorobenzene, a dichlorobenzene, fluoromethane, difluoromethane, trifluoromethane, 1-chloro-2,2-dimethylpropane, or combinations thereof.

13. The micro-emulsion of claim 1 wherein the co-solvent comprises an ether, an alcohol, an amide, an ester, a ketone, a nitrile, a sulfoxide, a sulfone or combinations thereof.

14. The micro-emulsion of claim 1, wherein the surfactant comprises a quaternary ammonium salt, a ternary ammonium salt, a phosphonium salt, a sulfonate salt, a sulfate salt, a phosphonate salt, a phosphate salt, a disubstituted amide, an ether, or a glyme.

15. The micro-emulsion of claim 14 wherein an anion of the quaternary ammonium salt, the ternary ammonium salt, or the phosphonium salt is the same as the halometallate anion or is compatible with the halometallate anion, or wherein a cation of the sulfonate salt, the sulfate salt, the phosphate salt or phosphonate salt is the same as the cation of the ionic liquid or is compatible with the cation of the ionic liquid.

16. The micro-emulsion of claim 1, wherein the catalyst promoter comprises an anhydrous hydrogen halide, a halogenated hydrocarbon, or combinations thereof.

17. A method of forming a micro-emulsion comprising:
   contacting a hydrocarbon, a co-solvent, an ionic liquid, a surfactant, and a catalyst promoter to form the micro-emulsion, the micro-emulsion comprising a hydrocarbon component comprising the hydrocarbon and an ionic liquid component comprising the ionic liquid, the ionic liquid comprising a halometallate anion and a cation, the co-solvent having a polarity greater than a polarity of the hydrocarbon, the co-solvent being miscible in the hydrocarbon, the co-solvent being present in an amount of about 30 wt % to about 80 wt % of the micro-emulsion, the ionic liquid being present in an amount of about 0.05 wt % to about 40 wt % of the micro-emulsion; wherein a molar ratio of the surfactant to the ionic liquid is less than 2.5:1, wherein a molar ratio of the catalyst promoter to the ionic liquid is 0.1:1 to 1:1, wherein the ionic liquid does not contain fluorine, wherein the micro-emulsion comprises micelles or reverse micelles and wherein more than about 90% of the micelles or reverse micelles have a diameter less than about 100 nanometers.

* * * * *